(12) United States Patent
Tourigny et al.

(10) Patent No.: US 9,733,229 B1
(45) Date of Patent: Aug. 15, 2017

(54) TEST KIT FOR DETECTING ACIDS IN REFRIGERANT LUBRICATING OILS AND METHOD OF USE

(71) Applicants: Jay S. Tourigny, Collinsville, CT (US); Wells Cunningham, New Hartford, CT (US)

(72) Inventors: Jay S. Tourigny, Collinsville, CT (US); Wells Cunningham, New Hartford, CT (US)

(73) Assignee: ZYNON TECHNOLOGIES, LLC, New Britain, CT (US)

( * ) Notice: Subject to any disclaimer, the term of this patent is extended or adjusted under 35 U.S.C. 154(b) by 579 days.

(21) Appl. No.: 14/208,790

(22) Filed: Mar. 13, 2014

Related U.S. Application Data (60) Provisional application No. 61/793,249, filed on Mar. 15, 2013.

(51) Int. Cl.
| | | |
|---|---|---|
| *G01N 33/28* | (2006.01) | |
| *G01N 21/80* | (2006.01) | |
| *G01N 31/22* | (2006.01) | |

(52) U.S. Cl.
CPC ......... *G01N 33/2888* (2013.01); *G01N 31/22* (2013.01); *G01N 21/80* (2013.01); *G01N 31/221* (2013.01)

(58) Field of Classification Search
CPC ...... G01N 31/221; G01N 21/77; G01N 31/22; G01N 21/80; G01N 33/2835; G01N 33/2876; G01N 33/2888; G01N 21/85; G01N 1/2035; G01N 2021/0193; G01N 2021/152; G01N 2021/8557; G01N 21/05; G01N 21/15; G01N 21/29; G01N 21/78; G01N 33/18; G01N 21/81; Y10T 436/15; Y10T 436/206664; Y10T 436/25375; F25B 49/005; F25B 2700/2116;
(Continued)

(56) References Cited

U.S. PATENT DOCUMENTS

| | | | |
|---|---|---|---|
| 2,826,060 A | 3/1958 | Gordon | |
| 4,203,725 A | 5/1980 | Snowden, Jr. et al. | |

(Continued)

FOREIGN PATENT DOCUMENTS

| | | |
|---|---|---|
| JP | 57-82763 A | 5/1982 |
| WO | 2012166760 A1 | 12/2012 |

*Primary Examiner* — John Fitzgerald
*Assistant Examiner* — Gedeon M Kidanu
(74) *Attorney, Agent, or Firm* — Cantor Colburn LLP (57) ABSTRACT

A test kit (110) includes an at least partially transparent or translucent tubular collection chamber (122) which has a flow control valve (111) at the inlet end (122a) thereof. Flow control valve (111) has a mouth (112a) that is used to engage a Schrader valve (132) of a HVACR system to flow pressurized refrigerant fluid into the collection chamber (122) via flow control valve (111). The flow of the pressurized refrigerant fluid is throttled by flow control valve (111) to ensure that sufficient lubricating oil is separated from the refrigerant fluid and remains within the collection chamber (122), even as refrigerant is expelled from collection chamber (122) via vent holes (124). A collector (126) serves to accumulate separated lubricating oil. A frangible ampoule (128) which contains a liquid pH indicator (130) is crushed to contact the pH indicator with the separated lubricating oil to test the pH of the oil by color change of the pH indicator.

26 Claims, 6 Drawing Sheets

(58) Field of Classification Search
CPC ............ F25B 2700/2117; F25B 31/002; F25B 2400/18; F25B 41/00; H01B 3/087
See application file for complete search history.

(56) References Cited

U.S. PATENT DOCUMENTS

| | | | |
|---|---|---|---|
| 5,139,049 A * | 8/1992 | Jensen | F16L 37/34 137/614.03 |
| 5,363,661 A * | 11/1994 | Condit | G01N 31/22 422/83 |
| 5,366,898 A | 11/1994 | Hagstrom et al. | |
| 5,377,496 A | 1/1995 | Otto et al. | |
| 5,419,177 A * | 5/1995 | Pastorello | G01N 1/2226 62/127 |
| 5,478,493 A | 12/1995 | Flaningam et al. | |
| 5,628,833 A | 5/1997 | McCormack et al. | |
| 5,707,871 A | 1/1998 | Sadhir et al. | |
| 5,773,403 A | 6/1998 | Hijino et al. | |
| 5,800,782 A * | 9/1998 | Hagstrom | G01N 31/16 422/537 |
| 5,834,416 A | 11/1998 | Morgan et al. | |
| 6,440,371 B1 * | 8/2002 | Dumitrescu | B01F 13/002 422/430 |
| 6,514,765 B1 * | 2/2003 | Scaringe | G01N 31/221 422/550 |
| 6,521,459 B1 * | 2/2003 | Schooley | G01N 33/2876 422/429 |
| 7,181,953 B1 * | 2/2007 | Street | G05D 16/103 137/505.25 |
| 7,284,412 B1 * | 10/2007 | Perrault | G01M 3/04 116/211 |
| 7,754,488 B2 | 7/2010 | Richardson et al. | |
| 2005/0227369 A1 * | 10/2005 | Richardson | G01N 21/78 436/169 |
| 2008/0206879 A1 | 8/2008 | Malone et al. | |

* cited by examiner

TEST KIT FOR DETECTING ACIDS IN REFRIGERANT LUBRICATING OILS AND METHOD OF USE

CROSS-REFERENCE TO RELATED APPLICATION

This application claims the benefit of priority of provisional patent application Ser. No. 61/793,249, filed on Mar. 15, 2013, entitled "Test Kit For Detecting Acids in Refrigerant Lubricating Oils and Method of Use".

BACKGROUND OF THE INVENTION

Field of the Invention

The present invention concerns apparatus, i.e., test kit devices, for testing the acidity of lubricating oils dispersed in the working fluid of heating, ventilation, air conditioning and refrigeration ("HVACR") systems, for example, the refrigerant of systems such as air conditioners, ice-making equipment, refrigerators, heat pump heating and cooling systems, and the like. The present invention also concerns methods of use of the aforesaid test kit devices.

HVACR systems employ Schrader valves to serve as access valves to inject refrigerant and/or oil into the system's refrigerant lines. The term "refrigerant lines" is used herein to refer to the working fluid transfer lines between the compressors and expansion units of HVACR systems. The Schrader valves may also be used to remove the contents of or samples from a system's refrigerant lines or to run tests on the lubricant oil for acid content. Each HVACR system typically has two Schrader valves, one located on the system high pressure side downstream of the compressor and upstream of the expansion unit, and the other on the system low pressure side downstream of the expansion unit and upstream of the compressor.

A Schrader valve consists of a machined valve body into which a valve core is threaded. The valve core is an assembly containing a spring, a movable core pin and a seating structure. The valve core is a service item that can be replaced and is suitably threaded for insertion into a refrigerant line access valve body to provide a normally closed valve arrangement. See *Air Conditioning, Heating and Refrigeration Institute* (formerly *Air Conditioning and Refrigeration Institute*) ARI Standard 720-97. The core pin in the access valve body can vary in its position depending on a number of variables including standard manufacturer recommended installation tolerances, wear and tear, and/or improper torques applied during valve core servicing. Every refrigerant system, small and large, contains at least one Schrader valve, which functions in a manner similar to the valve of an automobile tire. That is, depressing the core pin opens the valve to permit flow through the valve in either direction, depending on the respective pressures on either side of the valve.

Related Art

Refrigerant systems utilize lubricating oil which is mixed with the refrigerant fluid and thereby undergoes the same cyclic compression and expansion as the refrigerant. Generally, four different types or classes of lubricants are used in refrigerant systems. One class is mineral oil, another class is ester oil (which is based on the chemistry of polyol esters and is below referred to simply as "polyol ester oil"), the third class is polyalkaline glycol (PAG) oils and the fourth class is an alkylbenzene oil of the type commonly known as Zerol. The mineral oil is used for chlorofluorohydrocarbon ("CFC") refrigerants such as those sold under the trademark FREON, and hydrochlorofluorocarbon ("HCFC") refrigerants such as those designated R22. New refrigerants which are replacing CFCs and HCFCs are not soluble in mineral oil, so mineral oil is effectively being phased out along with the CFCs and HCFCs. Under the repeated compression and expansion cycles moisture or other impurities present in the system tend to chemically react with the lubricating oil to produce acidic reaction products. Even a very small amount of acid in the heat-transfer, e.g., refrigerant, system wreaks havoc on the system's equipment, most notably the system's compressor. Checking the system for acid is a routine maintenance procedure in large commercial air conditioning or refrigerant systems because, if detected early enough, acidic components can be economically removed from the system before the compressor or other parts of the system are irreparably damaged.

Title 40, Code of Federal Regulations ("CFR"), §608(c)(1), states that it is "unlawful for any person, in the course of maintaining, servicing, repairing or disposing of an appliance or industrial process refrigeration, to knowingly vent or otherwise knowingly release or dispose of any Class I or Class II substance used as a refrigerant in such appliance (or industrial process refrigeration) in a manner which permits such substance to enter the environment." However, the U.S. Environmental Protection Agency has issued "applicability determinations" that clarify that releases of refrigerant associated with oil sampling and testing are allowable under 608(c)(1) provided the release is "(a) less than one half ounce (14 grams) and (b) the duration of the test procedure from beginning to end, does not last more than 5 seconds."

The prior art discloses that litmus paper may be used in large systems to test the lubricant oil for acidity. However, litmus paper is not sensitive enough to provide a timely indication of low levels of acidic components present in the oil. By the time the litmus paper turns pinkish to indicate the presence of acid, the acid content is already high enough that the refrigerant system equipment has likely sustained significant damage. U.S. Pat. No. 6,514,765, issued Feb. 4, 2003 to Robert P. Scaringe et al., shows a hand-held test kit used to draw a refrigerant sample for testing and discloses the use of litmus paper and other acid color change papers positioned within the test kit. The color change papers are said to detect the presence of acids in the entrained oil of the refrigerant flowed over the color change paper.

The applicant's International Patent Publication WO 2012/166760 A1, published on 6 Dec. 2012 and entitled "Test Kit For Detecting Acids in Refrigerant Lubricating Oils and Method of Use" ("the '760 publication") discloses a test kit designed to have refrigerant from the Schrader valve of a refrigerant system flowed through it by pressing the device upon a conventional Schrader valve to collect a lubricating oil sample, as shown in FIG. 3 and described in paragraph [0046] of the '760 publication. Filters 13a and 13b, as shown in FIGS. 1-1D, and a frangible ampoule 14 containing a liquid pH indicator 16 are interposed within tube 12, which is transparent or translucent. The tube 12 is flexible enough to be compressed sufficiently to rupture frangible ampoule 14 to release the liquid pH indicator without rupturing flexible tube 12. See paragraphs [0031] and [0044]. Alternatively, as illustrated in FIG. 4 of the '760 publication, the liquid pH indicator may be added from exteriorly of the test device 10' by opening hinged end cap 18b'.

A difficulty encountered with such prior art flow-through test kits is that of "blow-through", that is, the pressure and velocity of the pressurized refrigerant is such that most of the entrained lubricating oil is carried out of the test kit with the refrigerant fluid, making it extremely difficult if not impossible to obtain even a small lubricating oil sample and to meet the sampling limitations of 40 CFR §608(c)(1). Prior art expedients include increasing the volume of the collection chamber of a test kit, introducing baffle means within the tube, extending the length of the tube and/or configuring the tube to provide a non-linear tortuous or baffled flow path. Insofar as the applicant is aware none of the known acid test kits adequately addresses the "blow-through" problem. In addition, some suffer from excessive cost and size. The test kit must be compact enough to be manipulated within the often limited confines of the refrigeration equipment.

Further, known test kits often require an oil sample size usually measured in multiple milliliters ("ml"), for example, 10 to 30 ml, approximately 10 to 30 grams. Withdrawing an amount of refrigerant to provide a lubricating oil sample of that size is technically feasible in large commercial refrigeration and air conditioning systems, even if not in compliance with 40 CFR §608(c)(1). However, taking such a large sample size is not feasible for smaller systems, such as small to medium capacity air conditioning units, household refrigerators, household and automotive air conditioning systems and the like.

Unless specifically otherwise stated or if the context clearly requires otherwise, as used herein and in the claims, the following terms shall have the indicated meanings whether used in singular or plural form.

The terms "lubricant" and "lubricating oil" are used interchangeably below and unless otherwise specified refer to the lubricating oil entrained in the refrigerant of a refrigeration system and to such lubricating oil collected as a sample within the test kit of the present invention.

The term "refrigerant" or "refrigerant fluid", unless otherwise specified, means broadly any compressible fluid suitable for use in a refrigerant system.

The term "fluid" shall mean and include a gas or vapor, a liquid, and mixtures of a gas or vapor with a liquid, and unless so specified does not exclude the presence of lubricating oil entrained in the fluid.

The term "refrigerant system" shall mean and include conventional refrigerant systems, air conditioning systems, heat pump heating and cooling systems, ice making systems, systems for cooling equipment and reactor vessels, and comparable systems in which a refrigerant is alternately compressed and expanded.

The term "effective test liquid" shall mean and include a combination of a pH indicator, for example, a liquid pH indicator, and lubricating oil to form a test liquid of such composition and such size as to show a discernable color change at a preselected acid pH.

The term "sufficiently transparent", as applied to the collection chamber of the test kit of the present invention, means fully transparent or translucent enough to enable observation of a discernable color change of the test liquid from exteriorly of the test kit.

A "flexible" or "collapsible" collection chamber, e.g., a tube, means a collection chamber which can be compressed, at least at a particular location thereof, sufficiently to crush an appropriately sized frangible ampoule disposed within the collection chamber, without rupturing the collection chamber or otherwise impairing the physical integrity of the collection chamber.

The term "disentrained" applied to lubricating oil means lubricating oil removed from the refrigerant or refrigerant fluid by flowing the refrigerant through the test kit of the present invention.

SUMMARY OF THE INVENTION

In accordance with the present invention, there is provided a highly sensitive test apparatus and method for detecting even very low levels of acidity in lubricants of refrigerant systems. The present invention requires only a very small size lubricant sample, may be used on small or large refrigerant systems, and overcomes the "blow-through" problem noted above.

In accordance with the present invention, there is provided a test kit for separating from a pressurized refrigerant withdrawn from a refrigerant system at least a portion of a lubricating oil entrained in the refrigerant to provide a lubricating oil sample, and then testing the lubricating oil sample for acidity. The test kit comprises the following components. A collection chamber having an interior wall and an observation location, and comprising an inlet end having an inlet-end opening and an outlet end having an outlet-end opening, the collection chamber defining a fluid flow path extending therethrough to the outlet-end opening. The inlet-end opening is configured to operate a system access valve of such pressurized refrigerant system to flow such refrigerant and its entrained lubricating oil via the inlet-end opening along the fluid flow path. A flow control valve is disposed in the fluid flow path to control the flow of refrigerant through the collection chamber, the flow control valve being configured to automatically throttle the flow of such pressurized refrigerant through the test kit to thereby enhance the retention of entrained lubricating oil within the collection chamber. Optionally, a collector body is disposed in the fluid flow path downstream of the flow control valve, the collector body being configured to collect thereon at least a portion of the lubricating oil sample. The collection chamber is configured to have dispensed therein a pH indicator, such as a liquid pH indicator, to mix with such oil sample to thereby form at the observation location a test liquid comprising a mixture of such oil sample and such pH indicator, the collection chamber being sufficiently transparent, at least at its observation location, so that visual observation of any color change which takes place in the test liquid may be observed from exteriorly of the test kit.

In one aspect of the present invention, the flow control valve comprises a control member which is displaceable from its closed position by the flow of such pressurized refrigerant through the flow control valve. In its closed position the control member prevents flow through the valve and in an open position permits such flow. The control member is operatively associated with a spring member which is configured to resist such displacement towards the open positions with a force which is proportional to the amount of such displacement towards the open positions, whereby the flow rate of such pressurized refrigerant through the flow control valve is attenuated.

In a related aspect of the present invention, the spring member is a coil spring which is compressed upon displacement of the control member towards the open position whereby the spring force of the coil spring resists displacement of the control member towards the open position.

Yet another aspect of the present invention provides for the flow control valve to comprise a mouth which is configured to engage such system access valve and a soft, resilient blow-back seal disposed in the mouth. The blow-back seal is sufficiently compressible and configured so as to accommodate both vertical movement and angular orientation of the test kit relative to the system access valve while establishing and maintaining a gas-tight seal between the test kit and the system access valve. The blow-back seal may have a durometer Shore A hardness of from about 2 to about 12, e.g., from about 2.5, 2.8 or 2.9 to about 5.

In accordance with a method aspect of the present invention, there is provided a method for separating lubricating oil from a pressurized refrigerant in which the lubricating oil is entrained, and testing the separated oil for acidity, the method comprising the following steps. (a) The pressurized refrigerant is introduced into a test kit comprising a collection chamber having (i) an inlet-end opening at or adjacent to which a flow-throttling flow control valve is disposed, and (ii) an outlet-end opening. The test kit defines a fluid flow path for the pressurized refrigerant, which flow path extends from the inlet-end opening to the outlet-end opening. (b) The pressurized refrigerant is flowed along the flow path and is discharged from the outlet-end opening; the flow of the pressurized refrigerant through the test kit is throttled by flowing the pressurized refrigerant through the flow control valve to thereby enhance retention within the collection chamber of a lubricating oil sample disentrained from the pressurized refrigerant; (c) a pH indicator, for example, a liquid pH indicator, is contacted with the lubricating oil sample to form a test liquid; and (d) any color change taking place in the test liquid is observed.

Another aspect of the method of the present invention provides that the collection chamber is sufficiently transparent at least at an observation location thereof, and further comprising the steps of: (d) after step (a) positioning the collection chamber to cause the separated oil to drain by gravity to the observation location, and after step (b) positioning the collection chamber to cause the pH indicator, for example, a liquid pH indicator, to drain by gravity to the observation location.

Still another aspect of the method of the present invention provides for a collector body to be disposed within the collection chamber downstream of the flow control valve, the method further comprising passing the pressurized refrigerant past the collector body to deposit at least some of the lubricating oil on the collector body.

Another method aspect of the invention provides for the collection chamber to have thereon a contact member, which may comprise the flow control valve, adjacent the inlet-end opening, and employing the contact member to operate the trigger of a valve of a pressurized refrigerant system to discharge the pressurized refrigerant into the collection chamber.

BRIEF DESCRIPTION OF THE DRAWINGS

FIGS. 1A-1E show, respectively, a perspective view (FIG. 1A), a side elevation view (FIG. 1B), an inlet end view (FIG. 1C-1) and an outlet end view (FIG. 1C-2) of one embodiment of the test kit of the present invention, with the internal components (except for the valve body) omitted to simplify the illustrations.

FIGS. 3-3C show, respectively, views of the valve body of FIG. 2, wherein FIG. 3 is a side view.

FIGS. 4, 4A and 4B show views, enlarged relative to FIG. 2, of a valve plunger usable as a component of the flow control valve of the test kit of FIGS. 1A-1E and of other embodiments of the present invention, wherein FIG. 4 is a side view.

FIGS. 5-5B respectively show views, enlarged relative to FIG. 2, of the control member 118 of the valve of FIG. 2, wherein FIG. 5 is a perspective view, FIG. 5A is a plan view and FIG. 5B is an elevation view;

DETAILED DESCRIPTION OF THE INVENTION AND SPECIFIC EMBODIMENTS THEREOF

Generally, the amount of lubricating oil in refrigerants used in refrigerant systems can range from a low of about 3% to as much as about 20% by weight of the combined weight of oil plus refrigerant. All references herein to expressions such as "wt %" or percent "by weight" of lubricating oil in a refrigerant means percentage by weight on the above-stated basis. If an acid test is conducted in accordance with the provisions of 40 CFR §608(c)(1) on refrigerant in a system containing as little as 3 wt % lubricating oil, the oil collected from one half ounce (14.175 grams) of refrigerant, assuming collection of all the oil, would be approximately 0.42 grams. As a practical matter, the oil sample will be smaller because less than all the lubricating oil present is collected. Therefore, the test kit must be capable of accurately testing a sample of lubricating oil as small as about 0.42 grams or less, for example, about 0.21 grams, assuming 50% of the oil is collected. The test kits of the present invention provide reliable test results with an oil sample size as low as 0.15 grams. The ideal amount of oil sample for pH testing is between 0.20 and 0.25 grams or higher, for example, about 0.5 grams. Therefore, the geometry of a test kit must be capable of collecting a sample of oil from no more than about one half ounce of refrigerant, and retain as much oil as feasible from the one half ounce of refrigerant. Prior art attempts to prevent the pressurized refrigerant from blowing the entrained oil out of the test kit (the "blow-through problem") have included increasing the internal volume of a test kit and/or configuring it to provide a tortuous and/or baffled refrigerant flow path. These attempts to retain a sufficient quantity of oil within the test kit have generally been unavailing, at least in a test kit small enough to be manipulated by hand within the confines of a refrigerant system.

Figures 1A, 1C, 1C:
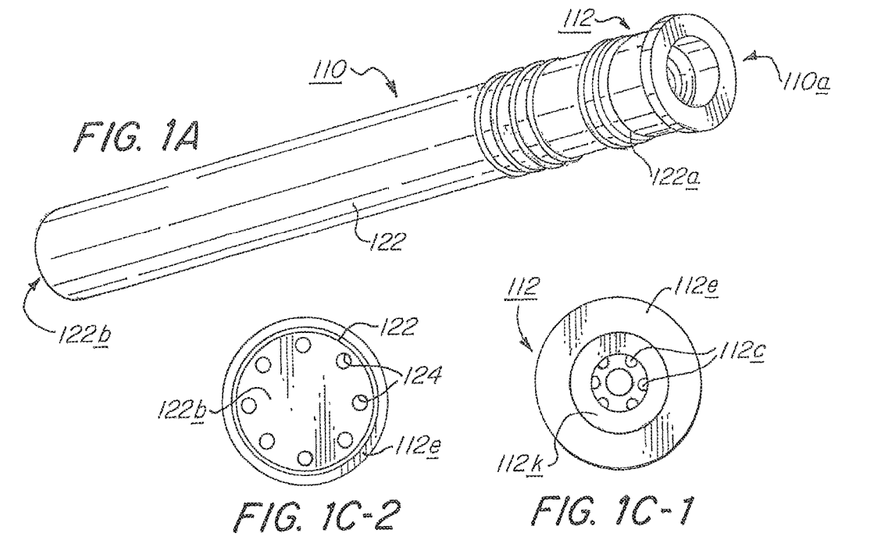
Figure 1B:
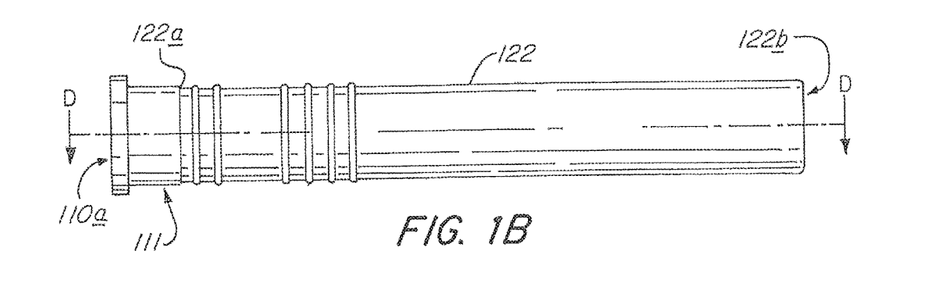

One embodiment of the test kit or apparatus of the present invention is shown in FIGS. 1A-1E wherein a test kit 110 has a flow control valve 111 mounted in the inlet end 122a of collection chamber 122 so that flow control valve 111 is disposed at the inlet end 110a of test kit 110. Collection chamber 122 has an opposite, outlet end 122b within which are formed a plurality of vent holes 124. Outlet end 122b is also the outlet end of test kit 110. Typical dimensions of a test kit of the present invention may be, for example, from about 4 to 5 inches in length (from inlet end 110a to outlet end 122b as shown in FIG. 1A) and an inside diameter of collection chamber 122 of about ½ inch to ⅝ inch. Obviously, any size test kit suited for a particular use may be employed. Collection chamber 122 is made of a sufficiently transparent, flexible, acid-free material such as a polyolefin marketed under the brand name "Engage 8402" by the Dow Chemical Company, or any suitable similar material. The described polyolefin or similar material is a low temperature resistant polymer that will maintain flexible properties and not split or otherwise degrade when exposed to sudden temperature drops consistent with being exposed to R22, R134a, R410a and other similar commercially available refrigerants found in HVACR systems.

Figure 1E:
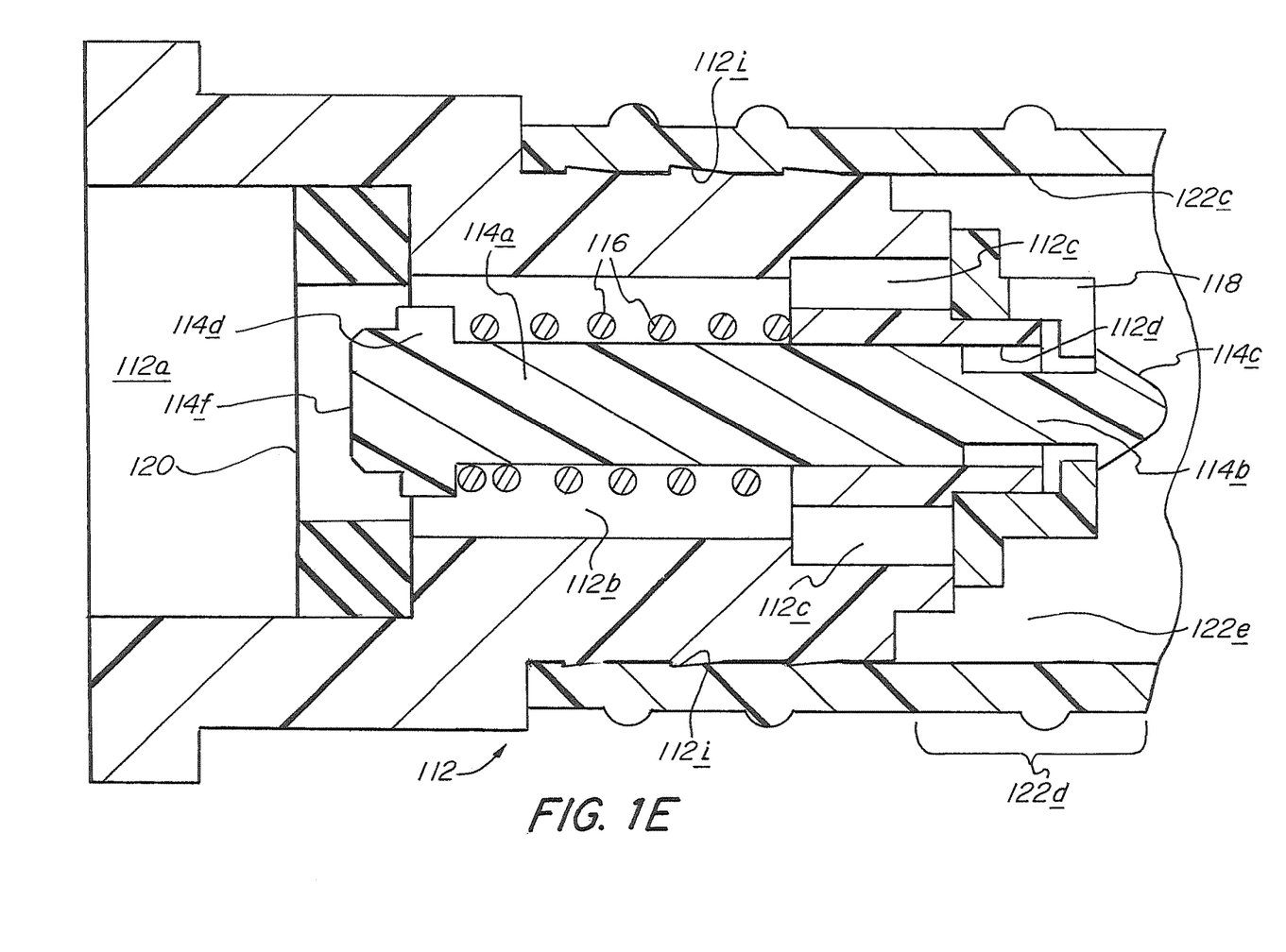
FIG. 1E is a view, enlarged relative to FIG. 1D, of the portion of FIG. 1D enclosed by the circle E.
Figure 2:
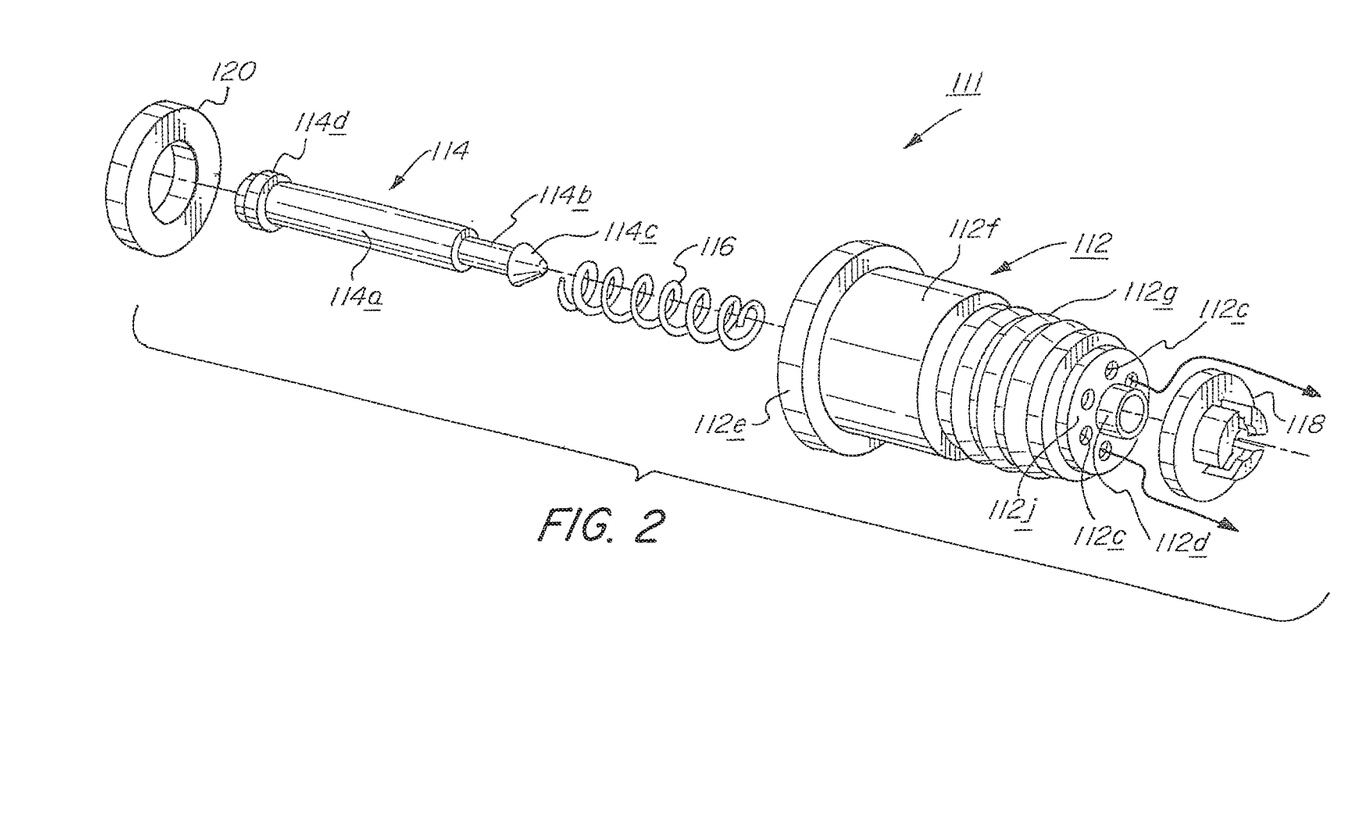
FIG. 2 is an exploded view of the flow control valve of FIG. 1D.

As best seen in FIG. 2, flow control valve 111 comprises a valve body 112, within or on which are a blow-back seal 120, a valve plunger 114, a coil spring 116 and a control member 118. As best seen in FIG. 1E, coil spring 116 is mounted on shaft 114a of valve plunger 114, which extends through valve body 112 with the shaft extension 114b and nose 114c protruding from valve body 112 to receive on shaft extension 114b a control member 118. A blow-back seal 120 (FIG. 1E) is provided in the illustrated embodiment by a soft, deformable and resilient washer or O-ring (not shown in FIG. 2) which is positioned in mouth 112a of flow control valve 111 adjacent to contact end 114d of valve plunger 114.

The following components are also disposed within collection chamber 122. A collector 126 is interposed between flow control valve 111 and a frangible ampoule 128, the latter of which is disposed between collector 126 and vent holes 124 of collection chamber 122. Collector 126 is comprised of a length of helical-shaped segments fastened to each other. Generally, any suitable convoluted structure may be used, such as a series of baffles or the like. A liquid pH indicator 130 is contained within frangible ampoule 128, which may be made of glass or any other frangible material such as a frangible polymer. Collection chamber 122, at least in the vicinity of frangible ampoule 128, is flexible, as more fully described below.

Figure 3:
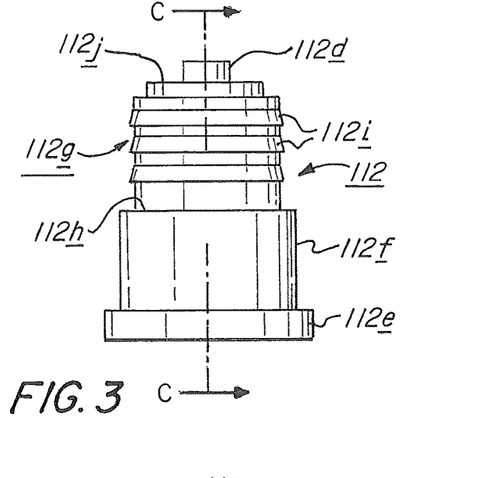
Figure 3A:
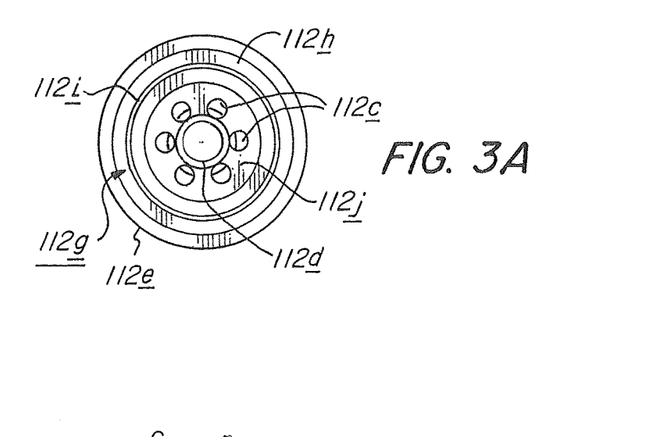
FIG. 3A is an end view of the valve discharge end.
Figure 3B:
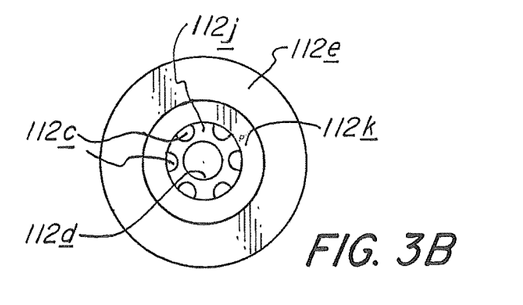
FIG. 3B is an end view of the valve intake end.
Figure 3C:
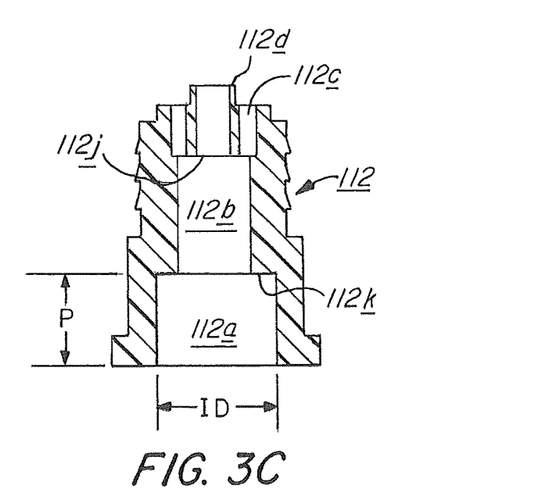
FIG. 3C is a cross-sectional longitudinal view taken along line C-C of FIG. 3.

Referring to FIGS. 2 and 3-3C, one of the components of flow control valve 111 is a valve body 112 which is of generally cylindrical configuration and has extending longitudinally through it a flow passage for a pressurized refrigerant fluid. Valve body 112 is preferably molded from a white material, such as a synthetic polymeric material, to provide good color contrast for observing any color change of the test liquid as described below. As best seen in FIG. 3C, the flow passage is comprised of a cylindrical-shaped mouth 112a, a cylindrical-shaped central passage 112b which is of smaller diameter than mouth 112a, and a plurality of still smaller diameter flow holes 112c (six in the illustrated embodiment) disposed circumferentially around a shaft bearing 112d. Central passage 112b terminates in an end wall 112j in which flow holes 112c and shaft bearing 112d are formed. The inside diameter of mouth 112a is indicated in FIG. 3C by dimension line ID and the depth of mouth 112a is indicated by dimension line P. The difference in diameter between mouth 112a and central passage 112b defines a circumferential internal shoulder 112k. The exterior of valve body 112 is configured to provide a base 112f from which a plug 112g extends. Base 112f is of larger diameter than plug 112g to define a circumferential shoulder 112h extending around the exterior of valve body 112. Plug 112g has flexible circumferential ribs 112i extending along most of its length to enhance friction fit and sealing when flow control valve 111 is inserted into the inlet end 122a of collection chamber 122. A circumferential flange 112e formed at the inlet end of base 112f is of slightly larger diameter than base 112f to enhance stability when the test kit is placed upright on a flat surface.

Figure 4:
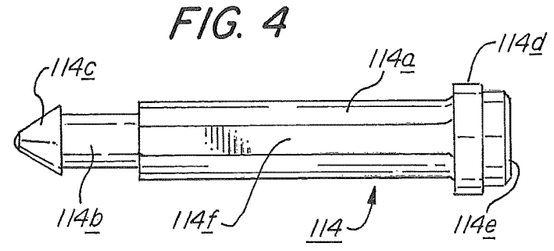
Figure 4A:
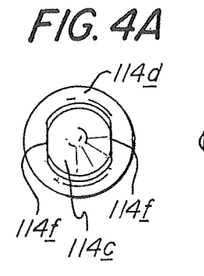
FIG. 4A is an end view of the nose end of the valve plunger.
Figure 4B:
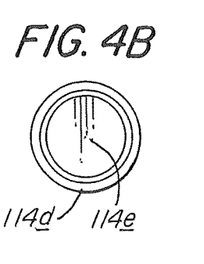
FIG. 4B is an end view of the contact end of the valve plunger.

Referring now to FIGS. 4-4B, valve plunger 114, as previously described, comprises a shaft 114a, shaft extension 114b, a nose 114c and a contact end 114d. Contact end 114d defines a contact face 114e and shaft 114a has flat faces 114f extending longitudinally along its entire length on diametrically opposite sides thereof. Contact face 114e is blunt to ensure good contact with the movable core pin 132c (FIG. 6) of a refrigerant system access valve 132. Contact end 114d is of larger diameter than shaft 114a to act as a stop for one end of the coil spring 116 as described below. Coil spring 116 is made of a corrosion and rustresistant material such as stainless steel. The opposite end of coil spring 116 is stopped against the end wall 112j of the valve body 112 (FIG. 1E). Nose 114c of valve plunger 114 is configured as a truncated cone to ensure precise positioning of the control member 118 against the base of nose 114c, which eliminates a possible variable during assembly and ensures that coil spring 116 is maintained at a consistent load from one test kit to the next. Valve plunger 114 is configured to have the control member 118 attached to it and held in place by means of an interference/snap fit and the spring load caused by the valve plunger 114 slightly compressing coil spring 116. Control member 118 is able to move freely along the cylindrical shaft extension 114b of the valve plunger 114. Control member 118 will be retained on shaft extension 114b by the base of nose 114c during operation of flow control valve 111, and when spring load is removed from the control member 118. Like the valve body 112, valve plunger 114 and control member 118 are molded, for example, from a synthetic polymer, or otherwise provided in the color white to assist in determining the color of the indicator test fluid during the test.

Figure 5:
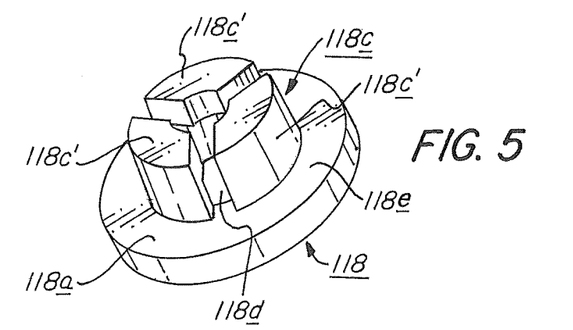
Figure 5A:
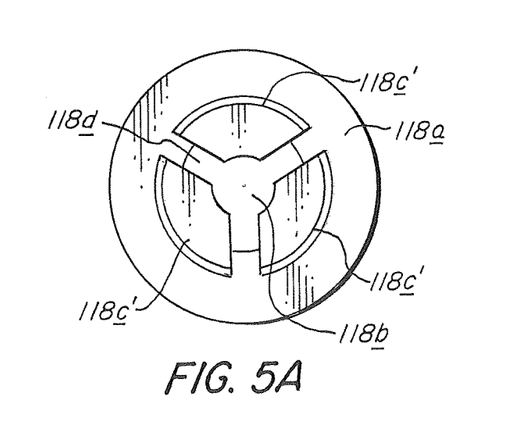
Figure 5B:
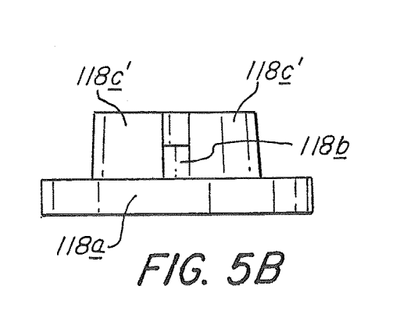

FIGS. 5-5B show that control member 118 has a washer-shaped base portion 118a through which a central opening 118b extends. A segmented cylinder 118c is comprised of three cylindrical segments 118c'. Control member 118 has two major design features that enhance test kit functionality; a wide diameter base portion 118a and a small diameter segmented cylinder 118c located on and extending from the downstream side of the base portion 118a. Base portion 118a is dimensioned to fit over the plurality of flow holes 112c in the end wall 112j of valve body 112 when the control member 118 is in the closed position, to prevent loss of fluids from the collection chamber during testing. The segmented cylinder 118c of control member 118 has therein three equally spaced-apart side cut openings 118e to allow material movement and recovery during interference/snap fit assembly of control member 118 with the valve plunger 114. The side cut openings define individual segments 118c' of cylinder 118c. Control member 118 (FIGS. 5-5B) and nose 114c (FIGS. 4-4B) cooperate to define a filler body disposed within the collection chamber 122 (FIG. 1D) at an observation location 122d (FIG. 1E) and spaced from interior wall 122c of the collection chamber. The filler body serves to displace the test liquid (lubricating oil sample plus pH indicator) into what may be referred to as an annular-shaped well 122e (FIG. 1E) bounded by the interior wall 122c of collection chamber 122 and the filler body. This displacement of the test liquid facilitates viewing the color of the test liquid through the wall of the collection chamber 122.

The assembly of the various components of flow control valve 111 is best appreciated from considering FIGS. 2 and 1E wherein it is seen that coil spring 116 is mounted on shaft 114a and is maintained thereon by one end of coil spring 116 bearing against the enlarged diameter portion of contact end 114d and the other end bearing on the interior side of end wall 112j. Valve plunger 114 is set in the valve body 112 so the control member 118 is positioned by the tension of coil spring 116 in the normally closed position, i.e., base portion 118a covers the flow holes 112c. When in the normally closed position, control member 118 (1) prevents contamination from entering the collection chamber 122 before, during and after use, (2) ensures that glass shards from the broken ampoule 128 do not escape through the flow holes 122c but remain safely in the collection chamber 122, and (3) prevents the test liquid (a mixture of lubricating oil sample and pH indicator) from leaking out of the test kit through the flow holes 122c during and after use.

Shaft extension 114b is received within shaft bearing 112 with nose 114c protruding beyond shaft bearing 112d. Shaft extension 114b extends through central opening 118b of control member 118 so that the base or larger diameter portion of nose 114c rests upon segments 118c' of segmented cylinder 118c. Insertion of the assembled flow control valve 111 into the inlet end 122a of collection chamber 122 provides a friction fit with the interior wall 122c of collection 122. The flexible ribs 112i ensure a tight friction fit with the interior wall 122c thereby avoiding the need for an adhesive, the presence of which might affect the color change reaction of the test liquid.

A deformable and resilient blow-back seal 120 is fitted within mouth 112a against interior shoulder 112k (FIG. 3C) and is sized to be force-fit within mouth 112a in which the deformable and resilient seal 120 is slightly compressed so that its resilience securely retains it in place. The blow-back seal 120 serves a number of functions. It prevents the loss of refrigerant discharged from the access valve 132 (FIG. 6) caused by backpressure which develops in the collection chamber 122 when drawing samples from the access valve 132. This is accomplished by blow-back seal 120 forming a seal between the leading edge 132b' of the threaded extension of access valve 132 (FIG. 6) and the test kit 110. The blow-back seal 120 is sufficiently thick and sufficiently soft and resilient to enable it to compensate for variations of the position of the core pin 132c of a given access valve 132, and still establish and maintain a gas-tight seal between the access valve 132 and the test kit 110. Compressibility of blow-back seal 120 gives test kit 110 an amount of vertical movement or "play" when engaging a given access valve, which play is equal to the difference between the uncompressed and compressed thickness of blow-back seal 120. This vertical play enables test kit 110 to accommodate any position of the core pin which lies within the range of core pin height variation normally encountered. In addition, the softness, resiliency and thickness of the blow-back seal 120 are sufficient to compensate for significant variations in the angle at which the acid test kit is oriented to the access valve 132 by the user. Blow-back seal 120 thus enables establishing and maintaining a gas-tight seal between test kit 110 and access valve 132 despite height position variations of core pin (132c) and deviations from vertical alignment of the test kit and access valve by the user. While the blow-back seal 120 may be made of any suitable material, one which has been successfully used is an acid-free expanded urethane, micropore foam material. One such material is the "Poron® Urethane Foam 4701-30" sold by Rogers Corporation of Woodstock, Conn. This product is available in three different densities of (a) 15, (b) 20 and (c) 25 lbs/ft³, with respective Shore A durometer hardnesses of (a) less than 3, e.g., 2 to 2.9, (b) 5 and (c) 12. The Shore A durometer hardness referred to herein is as determined by the test method of ASTM D 2240-97. Any one of these or comparable materials is believed to be suitable. The Shore A durometer hardness may be from about 2 to about 12, e.g., about 2.5 to about 6, or about 2.9 to about 5. The field-tested kits of Example 1 below used the 20 lbs/ft³ density Poron® material having a Shore A durometer hardness of about 5. A suitable thickness for blow-back seal 120 for a test kit whose valve body 112 has a mouth 112a (FIG. 1E or 3C) about 7/16 inch in diameter (dimension ID in FIGS. 3C and 6) and about 7/16 inch in depth (dimension P in FIG. 3C) is about 0.110 to 0.140 inches, e.g., 0.125 inch. The dimensions given for mouth 112a are typical for a test kit falling within the size range noted in paragraph [0039] above.

Figure 6:
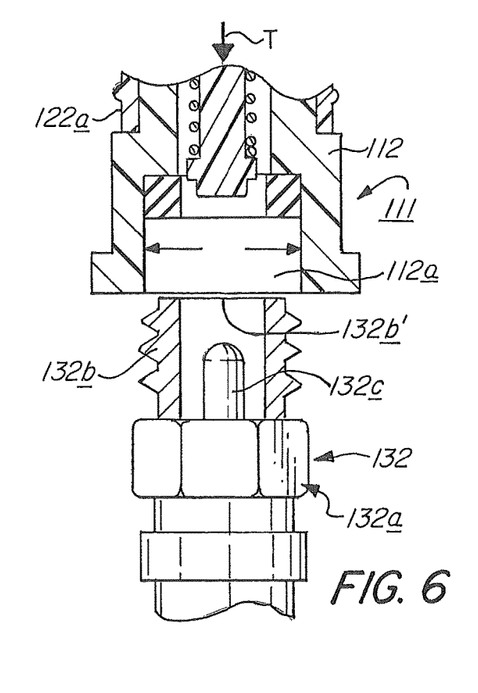
FIG. 6 is a partial cross-sectional elevation view of the test kit of FIGS. 1A-1E showing the inlet end of the test kit about to engage a conventional Schrader valve.

The sequence of operation is as follows. Referring to FIG. 6, the user positions the inlet end 110a of test kit 110 over an access valve 132 of a refrigerant system, and moves the test kit in the direction of arrow T to insert the mouth 112a of flow control valve 111 over valve 132, which typically is a Schrader valve. Access valve 132, as is typical, comprises an access valve body 132a having a threaded extension 132b within which is disposed a spring-loaded longitudinally moveable core pin 132c. The inside diameter (arrow ID in FIG. 6) of mouth 112a is sized to snugly and slidably fit over the threaded extension 132b of access valve 132, but is not threaded onto the threads. As test kit 110 is moved onto access valve 132, the contact end 114d of spring-loaded valve plunger 114 contacts core pin 132c and depresses it sufficiently to open access valve 132 to draw through it and into collection chamber 122 a sample of pressurized refrigerant containing entrained lubricating oil.

Figure 1D:
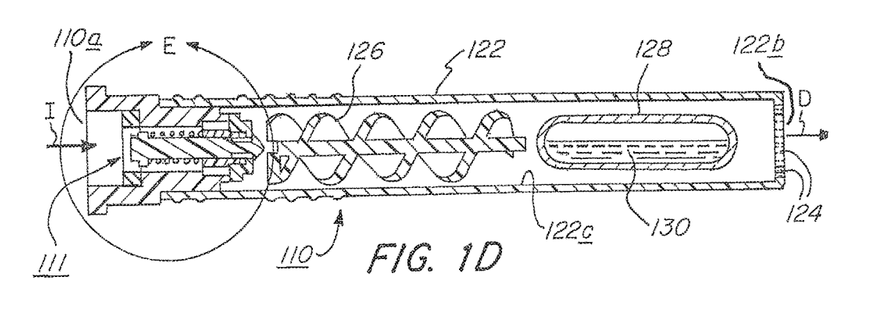
FIG. 1D is a cross-sectional view taken along line D-D of FIG. 1B and showing the internal components omitted from FIGS. 1A through 1C-2.

The pressurized refrigerant sample flows into flow control valve 111 as shown by arrow I in FIG. 1D and into the collection chamber 122, over and around collector 126 and ampoule 128 and now, somewhat depleted of its entrained lubricating oil, exits via vent holes 124 at outlet end 122b of collection chamber 122 in the direction shown by arrow D. A residue of lubricating oil disentrained from the refrigerant is left behind as a coating (not shown in the drawings) on collector 126, ampoule 128 and at least part of the interior wall 122c of collection chamber 122. When taking the test sample the vent holes 124 should be faced away from the operator to avoid spraying the operator with discharged refrigerant.

When control member 118 is in contact with end wall 112j of valve body 112, the valve is closed because base portion 118a is positioned directly over flow holes 122c to close them. Movement of control member 118 away from end wall 112j increasingly opens flow valve 111 for flow of pressurized refrigerant therethrough, exiting via flow holes 112c. The throttling action on the flow of pressurized refrigerant exerted by flow control valve 111 reduces the pressure and flow rate of refrigerant fluid through collection chamber 122, thereby enhancing the amount of lubricating oil which is disentrained, i.e., separated from, the refrigerant fluid and therefore trapped within collection chamber 122.

The pressurized refrigerant fluid flows through mouth 112a, central passage 112b, exits via flow holes 112c and impinges control member 118 with significant velocity and pressure. The impingement force urges control member 118 towards outlet end 122b, thereby increasing compression of coil spring 116 and reducing the force which coil spring 116 exerts on core pin 132c via valve plunger 114, thereby enabling core pin 132c to move partly, but not completely, towards its closed position. This in turn slows the velocity and reduces the flow volume of the pressurized refrigerant flowing into the test kit 110, thereby reducing the tendency of the pressurized refrigerant fluid to strip oil off the surfaces in the interior of collection chamber 122 and carry it out of the test kit 110, thereby ameliorating the "blow-through problem" referred to above.

Based on tests of randomly selected commercially available core sets of access (Schrader) valves offered by various manufacturers, and by tests of such access valves on operating HVACR systems, the preferred spring rate for the coil spring 116 is about 2½ to 3 pounds at 35% compression of the spring.

Further, increased compression of coil spring 116 urges valve plunger 114, and therefore control member 118, to move in the direction of closing flow control valve 111, thereby adding to the beneficial throttling of flow of the refrigerant fluid. As may best be appreciated from FIG. 2, as control member 118 is urged towards its closed position, the refrigerant fluid passing through flow holes 112c is constrained to flow through a smaller opening and is diverted from a linear flow path (as shown by the unnumbered arrows in FIG. 2) as it enters collection chamber 122. The higher the pressure of the refrigerant fluid introduced into test kit 112, the more coil spring 116 will be compressed and the stronger will be the force which coil spring 116 exerts in urging control member 118 towards its closed position.

As an added benefit, the turbulence caused in the flow of the refrigerant fluid by the control member 118 speeds the transition of any liquid component of the refrigerant fluid into a gas, which facilitates leaving lubricant oil behind in the collection chamber 122.

After the sample is taken and test kit 110 is removed from the Schrader valve, frangible ampoule 128 is crushed by squeezing collection chamber 122 in the vicinity of ampoule 128 to release the liquid pH indicator 130. Collection chamber 122, at least in the vicinity of ampoule 128, is sufficiently flexible that the operator may squeeze that portion of collection chamber 122 sufficiently to crush frangible ampoule 128 without rupturing collection chamber 122. The physical integrity of collection chamber 122 is thereby maintained to avoid spillage, or contamination of the contents of, collection chamber 122. The test kit 110 may be shaken or swirled to thoroughly mix liquid pH indicator 130 with the oil sample (not shown in the drawings) collected within collection chamber 122. The test kit 110 is then held or placed in an upright position, that is, with outlet end 122b positioned vertically above inlet end 122a, so that the mixture of collected oil sample and the liquid pH indicator 130 drains downwardly by gravity and collects at observation location 122d (FIG. 1E) in the vicinity of control member 118 of flow control valve 111. Collection chamber 122 is made sufficiently transparent at least at observation location 122d. In this way, any color change which takes place when liquid pH indicator 130 mixes with the lubricating oil trapped within collection chamber 122 to form a test liquid (not shown in the drawings) may readily be observed by the operator.

The acid test kit 110 must be capable of depressing core pin 132 of the access valve 132 sufficiently to dispense pressurized refrigerant into the test kit. This is achieved in the acid test kit of the present invention through the use of a valve actuation assembly, which may advantageously be provided by the flow control valve. The core spring 116 on the valve plunger 114 is set to a tension that closely matches the tension of the spring-loaded movable core pin 132c of the access valve 132. The spring-assisted valve plunger 114 overcomes the spring-loaded tension in the core pin 132c of the HVACR access valve 132 and causes the normally closed valve 132 to slightly open. Variations in the position of core pin 132b are compensated for as described in paragraph [0046] above.

Figure 7:
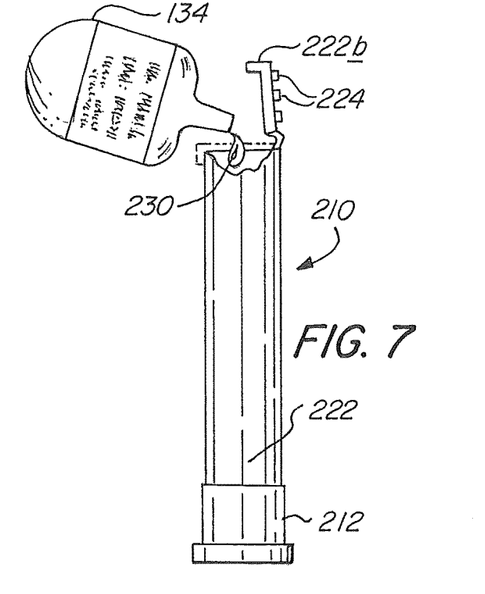
FIG. 7 is a schematic elevation view of a third embodiment of the test kit of the present invention.

FIG. 7 illustrates another embodiment of the invention comprising a test kit 210 having a collection chamber 222. The internal components of test kit 210 are not shown in FIG. 7 except for a portion of valve body 212 protruding therefrom. In the embodiment of FIG. 7, outlet end 222b of collection chamber 222 has vent holes 224 formed therein and is hinged so that it may be moved to an open position shown in FIG. 7 and then returned to a closed position as indicated by the phantom outline of outlet end 222b in FIG. 7. A snap-fit of outlet end 222b seals collection chamber 222. With outlet end 222b in the open position shown in FIG. 7, a liquid pH indicator 230 may be dispensed from a suitable container 134 to add a precisely controlled amount of liquid pH indicator into collection chamber 222. In this embodiment, it is not necessary that collection chamber 222 have a flexible portion. Generally, however, the embodiment of FIGS. 1-1E is preferred because use of a frangible ampoule enables factory addition of a precisely controlled amount of liquid pH indicator.

Example 1

A. The ability of test kits of the present invention to collect oil samples was tested in collection field trials of 93 test kits in accordance with the embodiment of the present invention illustrated in FIGS. 1A-6. The collection tests were performed on a variety of commercial and residential systems using either R-22 or R-410a refrigerant. The test procedure was to press, as illustrated in FIG. 6, the valve actuation portion of the test kit (the mouth 112a of valve body 112) on an access (Schrader) valve located on the low pressure side of an operating system for 5 bursts of ½ second each. The results varied and were found to be dependent on the elevation of the Schrader access valve in respect to other parts of the system. The entrained lubricating oil tends to be concentrated in the lowest elevation point of the system, which is not always where the low pressure side Schrader valves are located. As a result, it is possible to not collect any oil in some systems where the sampled access valve is significantly elevated above the rest of the system.

B. The test results are summarized as follows:
Highest oil collection weight=0.6965 grams
Lowest oil collection weight=0 grams
Average oil collection weight (including zero oil collections)=0.1639 grams
Average oil collection weight (excluding zero oil collections)=0.2021 grams.

Thirty-three of the tests collected significantly more oil than the minimum of about 0.15 grams needed for testing and thirty of the tests collected more than an adequate amount of oil for testing. Thirty tests collected no discernible amount of oil. The sites of the access valves which yielded zero oil collections are believed to be oil-starved and this indicates that remedial measures may have to be taken, especially if the oil-starved site is upstream a small distance from critical equipment such as a compressor. It is believed that Schrader valve sites which are at higher elevations than the rest of the refrigerant system tend to have a lower concentration of entrained lubricating oil than those portions of the system at lower elevations.

C. The total duration of collection of 2½ seconds (5 bursts of ½ second each) is well within the maximum of five seconds duration permitted under 40 CFR §608(c)(1). Even at a low entrained oil content of 5% by weight oil, the highest collected oil weight of 0.6965 grams would require only 13.93 grams of refrigerant, just within the maximum 14 grams permitted under 40 CFR §608(c)(1). At the lowest safe lubricating oil content of 3% by weight oil, the average weight (including zero oil collections) of 0.1639 grams of collected oil would require only 8.29 grams of refrigerant. Modern HVACR systems usually include an access valve at a low elevation section of the system in addition to an access valve or valves at higher elevations of the system. Provision of a low elevation access valve facilitates obtaining a lubricating oil sample.

Example 2

A. Color change reactions were tested as follows. A phenolphthalein-TIA test liquid was adjusted to show a color change at an acid number of 0.05 mg KOH/gram sample. This will convert the indicator to a noticeably lighter purple or rose color or green or clear yellow liquid within several minutes. This color change signifies the presence of enough acid in a mineral oil lubricant to cause the onset of damage to the compressor of a refrigerant system. Stated otherwise, mineral oil lubricants can sustain acid numbers of less than 0.05 mg KOH before the onset of compressor damage. On the other hand, polyol ester oil lubricants can sustain acid numbers of less than 0.16 mg KOH/gram of sample before the onset of compressor damage. With an acid number of 0.16 mg KOH/gram of sample, the same adjusted phenolphthalein test liquid will cause the color change to be immediate and render the test liquid completely colorless. A strip of colors showing color changes representative of various acid numbers when using the liquid pH indicator in the test kit may be provided. This will enable the operator, whether experienced or not, to more easily determine whether at least the threshold level of acid is present in the oil residue, regardless of the type of lubricant oil tested. The threshold level of acid is the amount of acid which will prove deleterious to the refrigeration equipment whose lubricating oil is being tested. This enables ascertaining when the tolerable level of acid has been reached or exceeded. This technique allows the use of a single standard type test kit for any kind of present or future lubricant to test for any acid number over a significant range of acid numbers. The test kit of the present invention has been found to detect acid levels as low as 0.05 mg/gm acid number in mineral oil and as low as 0.16 mg/gm acid number in polyol ester oil and in alkylbenzene oil.

B. A series of tests was carried out utilizing a liquid pH indicator comprising:
Phenolphthalein 11.2 wt % of a 1% solution in denatured ethyl alcohol
Toluene 56.1 wt %
Isopropyl alcohol 30.0 wt %
The pH was adjusted by the addition of 2.7 wt % of a solution of 0.1N KOH in isopropanol.

C. Phenolphthalein was selected as a pH indicator because in the pH range of interest, the combination of phenolphthalein with the toluene and isopropyl alcohol solvent/carrier liquid provided the darkest hue of any other phenolphthalein test liquid tested. Of course, any other suitable pH indicators, such as bromothymol blue, or bromophenol blue, may of course be used. Similarly, other suitable solvent/carrier liquids such as xylene, chlorinated or brominated hydrocarbons, N-methyl pyrrolidone or ethyl acetate or suitable mixtures of two or more thereof may of course be used, in combination with suitable ones or combinations of the pH indicators.

D. Test and control lubricant oils in volumes of 0.5 ml were tested. The weight percents are based on the weight of the additive as a percentage of weight of the total mixture.
Test Lubricant Oils
A. Mineral oil containing 268 ppm by weight of oleic acid was prepared to provide an acid number of 0.053 mg/gm.
B. Polyol ester oil containing 177 ppm by weight of acetic acid was prepared to provide an acid number of 0.165 mg/gm.
C. Alkylbenzene oil containing 52 ppm by weight of acetic acid was prepared to provide an acid number of 0.049 mg/gm.
Control Lubricant Oils
A'. Unused mineral oil, no acid added.
B'. Unused polyol ester oil, no acid added.
C'. Unused alkylbenzene oil, no acid added.
Each test and control lubricant oil in 0.5 ml aliquots were mixed in separate, clean test tubes with 0.5 ml of the phenolphthalein-TIA test liquid, which had a dark purple color. The following results were attained after 30 seconds of reaction time with swirling of the mixed liquids, and then observing the color after 3 to 5 minutes of settling.

| Test Lubricant Oil | Result | Control Lubricant Oil | Result |
|---|---|---|---|
| A | light rose | A' | No color change |
| B | colorless immediately | B' | No color change |
| C | colorless after 5 minutes | C' | No color change |

Example 3

Use of an indicator mixture which is sensitive to lower amounts of acidic oil was tested. A series of tests was carried out utilizing a liquid pH indicator comprising:
Phenolphthalein (solid) 1.00 wt %
Bromothymol blue (solid) 0.19 wt %
Toluene 61.08 wt %
Isopropyl alcohol 32.00 wt %
The pH was adjusted by the addition of 5.73 wt % of a solution of 0.1N KOH in isopropanol. Each test and control lubricant oil in 0.1 ml aliquots was added to an indicator test kit with an ampoule of 0.25 ml of the test liquid, which had a light navy blue color. The test kit was capped, the ampoule cracked and the kit shaken to mix the oil and the fluid. Within one minute the following results were obtained.

| Test Lubricant Oil | Result | Control Lubricant Oil | Result |
|---|---|---|---|
| A | forest green | A' | Blue |
| B | yellow-green | B' | Blue |

Figure 8:
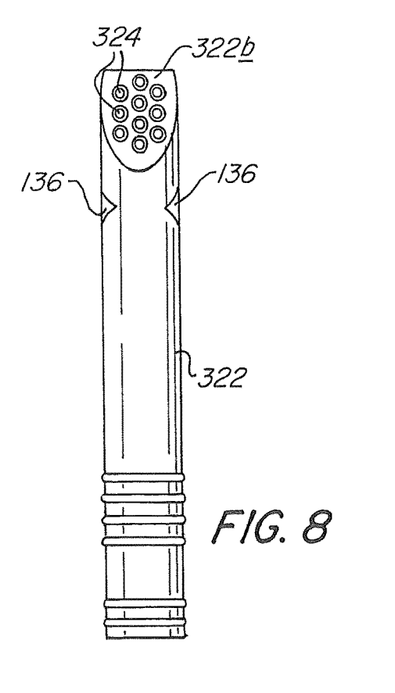
FIG. 8 is a front elevation view of a collection chamber in accordance with another embodiment of the present invention, which is usable as a component of the test kit of FIGS. 1A-1E and of other embodiments of the present invention.
Figure 9:
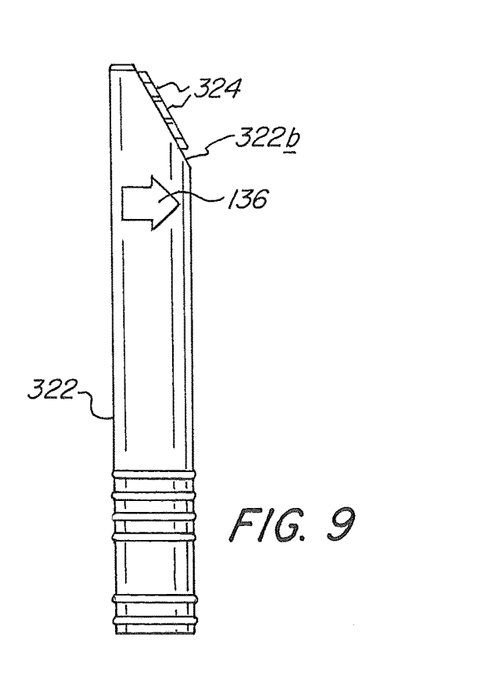
FIG. 9 is a side elevation view of the collection chamber of FIG. 8.

FIGS. 8 and 9 illustrate an alternate embodiment of a collection chamber usable in the present invention wherein collection chamber 322 differs from collection chamber 122 of the embodiment of FIGS. 1-1E substantially only in that outlet end 322b is disposed at an acute angle to the longitudinal axis of collection chamber 322. In this embodiment, the plurality of vent holes 324 on the angled outlet end 324 are configured with raised nozzles to direct the discharge gasses at a right angle direction relative to the longitudinal axis of collection chamber 322. In all configurations, the plurality of vent holes 124, 224 and 324 on the respective outlet or discharge ends of the collection chambers 122, 222 and 322 are sized to retain and prevent loss of glass particles that result from the frangible ampoule 128 being broken to release the pH indicator. Arrow indicia 136 are formed on the outer surface of collection chamber 322 to indicate the direction in which pressurized refrigerant fluid will be discharged from vent holes 324, to alert the operator to position the test kit correctly when drawing a sample of the pressurized refrigerant fluid.

A test kit in accordance with the present invention may also include instructions and a color strip. The color strip correlates an acid number to different shades of the reacted liquid pH indicator which enables the operator to match the post-test color of the liquid pH indicator to facilitate assessing the acid number of the tested lubricating oil.

While the invention has been described in connection with certain specific embodiments thereof, it will be appreciated that numerous variations may be made to the described specific embodiments which variations nonetheless lie within the spirit and scope of the present invention.

What is claimed is:

1. A test kit for separating from a pressurized refrigerant withdrawn from a refrigerant system at least a portion of a lubricating oil entrained in the refrigerant to provide a lubricating oil sample, and then testing the lubricating oil sample for acidity, the test kit comprising:
    a collection chamber having an interior wall and an observation location, and comprising an inlet end having an inlet-end opening and an outlet end having an outlet-end opening, the collection chamber defining a fluid flow path extending therethrough to the outlet-end opening, the inlet-end opening being configured to operate a system access valve of such pressurized refrigerant system to flow such refrigerant and its entrained lubricating oil via the inlet-end opening along the fluid flow path;
    a flow control valve disposed in the fluid flow path and configured to automatically throttle the flow of such pressurized refrigerant through the collection chamber to thereby enhance both (1) separation of some of the entrained lubricating oil from the pressurized refrigerant to provide the lubricating oil sample as a liquid lubricating oil, and (2) retention of the liquid lubricating oil sample within the collection chamber;
    the collection chamber being configured to have dispensed therein a pH indicator to mix with such liquid oil sample to thereby form at the observation location a test liquid comprising a mixture of such liquid oil sample and such pH indicator, the collection chamber being sufficiently transparent at least at the observation location whereby visual observation of any color change which takes place in the test liquid may be observed from exteriorly of the test kit.

2. The test kit of claim 1 further comprising a collector body disposed within the collection chamber in the fluid flow path downstream of the flow control valve, the collector body being configured to collect thereon at least a portion of the liquid lubricating oil sample.

3. The test kit of claim 1 further comprising a filler body disposed within the collection chamber at the observation location and spaced from the interior wall of the collection chamber to thereby define between the interior wall and the filler body an annular well which is configured to receive such test liquid.

4. The test kit of claim 1 wherein such system access valve comprises a core pin which, when displaced, serves to open such system valve, and the flow control valve is disposed at the inlet end of the collection chamber and comprises a spring-loaded valve plunger which is configured to contact and displace such core pin when the inlet end of the collection chamber is placed over such system valve.

5. A method for separating lubricating oil from a pressurized refrigerant in which the lubricating oil is entrained, and testing the separated oil for acidity, the method comprising:
    (a) introducing the pressurized refrigerant into a test kit comprising a collection chamber having an inlet-end opening at or adjacent to which a flow-throttling flow control valve is disposed, and an outlet-end opening, the test kit defining a fluid flow path for the pressurized refrigerant, the fluid flow path extending from the inlet-end opening to the outlet-end opening;
    (b) flowing the pressurized refrigerant along the flow path and discharging the pressurized refrigerant from the outlet-end opening, and throttling the flow of the pressurized refrigerant through the test kit by flowing the pressurized refrigerant through the flow control valve, to thereby enhance retention within the collection chamber of a liquid lubricating oil sample disentrained from the pressurized refrigerant;
    (c) contacting a pH indicator with the liquid lubricating oil sample to form a test liquid; and
    (d) observing any color change taking place in the test liquid.

6. The test kit of claim 1 or claim 2 wherein the outlet-end opening is comprised of a plurality of gas vent holes formed in the outlet end.

7. The test kit of claim 6 wherein the collection chamber has a longitudinal axis and the outlet end is disposed at an acute angle to the longitudinal axis whereby to direct refrigerant discharged through the outlet end at a right angle direction relative to the longitudinal axis.

8. The test kit of claim 1 or claim 2 wherein the flow control valve comprises a mouth which is configured to engage such system access valve and a soft, resilient blow-back seal disposed in the mouth, the blow-back seal being sufficiently compressible and configured so as to accommodate both vertical movement and angular orientation of the test kit relative to the system access valve while establishing and maintaining a gas-tight seal between the test kit and the system access valve.

9. The test kit of claim 8 wherein the blow-back seal has a durometer Shore A hardness of from about 2 to about 12.

10. The test kit of claim 8 wherein the blow-back seal has a durometer Shore A hardness of from about 2.5 to about 5.

11. The test kit of claim 1 or claim 2 further comprising a pH indicator disposed within the collection chamber.

12. The test kit of claim 11 wherein the flow control valve is disposed at the inlet end of the collection chamber and the collector body is disposed between the flow control valve and the outlet end.

13. The test kit of claim 11 further comprising a frangible ampoule disposed within the collection chamber, which ampoule contains the pH indicator in liquid form, and wherein the collection chamber has a collapsible portion at least in the location thereof within which the ampoule is disposed, whereby the ampoule may be crushed by squeezing the collapsible portion of the collection chamber to release the pH indicator within the collection chamber.

14. The test kit of claim 1 or claim 2 wherein the collection chamber comprises a closeable access opening through which such pH indicator may be introduced into the collection chamber.

15. The test kit of claim 14 wherein the closeable access opening is closeable by a cap having therein a plurality of gas vent holes which gas vent holes serve as the outlet-end opening.

16. The test kit of claim 14 further comprising a storage receptacle disposed exteriorly of the collection chamber and such pH indicator comprises a quantity of a liquid pH indicator disposed within the storage receptacle, and wherein the storage receptacle is configured to enable deposition therefrom of the liquid pH indicator into the collection chamber.

17. The test kit of claim 1 or claim 2 wherein the flow control valve comprises a control member which is displaceable by the flow of such refrigerant through the flow control valve from a closed position which prevents flow through the valve to open positions which permit flow through the valve, the control member being operatively associated with a spring member which is configured to resist such displacement towards the open positions with a force which is proportional to the amount of such displacement towards the open positions, whereby the flow rate of such pressurized refrigerant through the flow control valve is attenuated.

18. The test kit of claim 17 wherein the flow control valve has a nose portion and the filler body is comprised of the nose portion and the control member.

19. The test kit of claim 17 wherein the control member is operatively associated with a coil spring which is compressed upon displacement of the control member towards the open positions whereby the spring force of the coil spring resists such displacement of the control member towards the open positions.

20. The test kit of claim 19 wherein the control member has a plate-like configuration and is so disposed in the flow path to deflect such pressurized refrigerant flowing through the flow control valve into a change of flow direction.

21. The test kit of claim 1, claim 2 or claim 5 wherein the pH indicator comprises a liquid pH indicator.

22. The method of claim 5 wherein the collection chamber is sufficiently transparent at least at an observation location thereof and further comprising the steps of:
  (e) after step (b), positioning the collection chamber to both (1) cause the lubricating oil sample to drain by gravity to the observation location, and (2) to carry out step (c) by causing the pH indicator to also drain by gravity to the observation location.

23. The method of claim 5 or claim 22 wherein a collector body is disposed within the collection chamber downstream of the flow control valve and the method further comprises passing the pressurized refrigerant past the collector body to deposit at least some of the disentrained lubricating oil sample on the collector body.

24. The method of claim 5 or claim 22 wherein the pH indicator is a liquid pH indicator.

25. The method of claim 5 or claim 22 wherein the collection chamber has thereon a contact member adjacent the inlet-end opening, and employing the contact member to operate the core pin of a valve of a pressurized refrigerant system to discharge the pressurized refrigerant into the collection chamber.

26. The method of claim 25 further comprising employing the control valve as the contact member.

* * * * *